United States Patent [19]

Lange et al.

[11] Patent Number: 4,588,434
[45] Date of Patent: May 13, 1986

[54] SUBSTITUTED UREAS AND THEIR USE FOR CONTROLLING UNDESIRABLE PLANT GROWTH

[75] Inventors: Arno Lange, Bad Durkheim; Bruno Wuerzer, Otterstadt, both of Fed. Rep. of Germany

[73] Assignee: BASF Aktiengesellschaft, Fed. Rep. of Germany

[21] Appl. No.: 559,181

[22] Filed: Dec. 7, 1983

[30] Foreign Application Priority Data

Dec. 10, 1982 [DE] Fed. Rep. of Germany ....... 3245679

[51] Int. Cl.⁴ .................. A01N 37/00; C07C 153/023
[52] U.S. Cl. ...................................... 71/100; 558/251; 558/257
[58] Field of Search ........................ 260/455 R; 71/100

[56] References Cited

U.S. PATENT DOCUMENTS 4,067,726 1/1978 Sasse et al. ........................... 71/120

FOREIGN PATENT DOCUMENTS 1451299 9/1976 United Kingdom ............ 260/455 R

Primary Examiner—Henry R. Jiles
Assistant Examiner—Robert C. Wittenbaugh
Attorney, Agent, or Firm—Keil & Weinkauf

[57] ABSTRACT

Substituted ureas of the formula

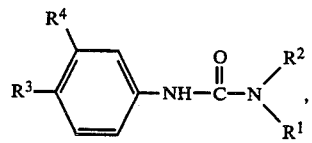

where $R^1$ is hydrogen or alkyl, $R^2$ is hydrogen, alkyl, alkoxy, alkenyl, alkynyl, unsubstituted or substituted cycloalkyl or unsubstituted or substituted phenyl and $R^3$ and $R^4$ are each hydrogen, halogen or a radical —CO—S—R, with the proviso that one or both of the substituents $R^3$ and $R^4$ are the radical —CO—S—R, are used for controlling undesirable plant growth.

10 Claims, No Drawings

SUBSTITUTED UREAS AND THEIR USE FOR CONTROLLING UNDESIRABLE PLANT GROWTH

The present invention relates to substituted ureas, herbicides which contain these compounds, and methods of controlling undesirable plant growth using these compounds.

It has been disclosed that alkoxycarbonylphenylureas possess herbicidal activity (German Laid-Open Applications DOS No. 2,413,258 and DOS No. 2,445,529).

We have found that substituted ureas of the formula

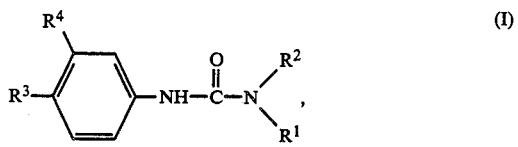

where $R^1$ is hydrogen or $C_1$-$C_4$-alkyl, $R^2$ is hydrogen, $C_1$-$C_4$-alkyl, $C_1$-$C_4$-alkoxy, $C_2$-$C_4$-alkenyl, $C_2$-$C_4$-alkynyl, unsubstituted or $C_1$-$C_4$-alkyl-substituted $C_3$-$C_7$-cycloalkyl, or phenyl which is unsubstituted or substituted by halogen or by $C_1$-$C_4$-haloalkyl, $R^3$ is hydrogen, halogen or a radical —CO—S—R where R is $C_1$-$C_{10}$-alkyl, $C_3$-$C_8$-cycloalkyl, $C_2$-$C_4$-alkenyl, $C_2$-$C_4$-alkynyl or $C_7$-$C_{12}$-aralkyl and $R^4$ is hydrogen, halogen or a radical —CO—S—R, where R is $C_1$-$C_{10}$-alkyl, $C_3$-$C_8$-cycloalkyl, $C_2$-$C_4$-alkenyl, $C_2$-$C_4$-alkynyl or $C_7$-$C_{12}$-aralkyl, with the proviso that one or both of the substituents $R^3$ and $R^4$ are —CO—S—R, possess substantial herbicidal activity and are surprisingly well tolerated by a number of crops.

In formula I, $R^1$ is hydrogen or $C_1$-$C_4$-alkyl, eg. methyl, ethyl, n-propyl or i-butyl, preferably methyl or ethyl, $R^2$ is hydrogen, $C_1$-$C_4$-alkyl, $C_1$-$C_4$-alkoxy, $C_2$-$C_4$-alkenyl, $C_2$-$C_4$-alkynyl or $C_3$-$C_7$-cycloalkyl which is unsubstituted or substituted by $C_1$-$C_4$-alkyl, preferably by methyl, or is phenyl which is unsubstituted or substituted by halogen, preferably chlorine, or by $C_1$-$C_4$-haloalkyl, eg. methyl, ethyl, n-propyl, isopropyl, tert.-butyl, methoxy, ethoxy, vinyl, prop-1-en-4-yl, ethynyl, propyn-1-yl, propargyl, but-2-yn-1-yl, but-1-yn-3-yl, but-1-yn-4-yl, 3-methylbut-1-yn-3-yl, cyclopropyl, cyclobutyl, cyclopentyl, cyclohexyl, 2-methylcyclohexyl, 3,4-dichlorophenyl or 3-trifluoromethylphenyl, preferably methyl or ethyl.

In the radical —CO—S—R, which may be $R^3$ or $R^4$ in formula I, R is $C_1$-$C_{10}$-alkyl, preferably $C_4$-$C_8$-alkyl, or $C_3$-$C_8$-cycloalkyl, $C_2$-$C_4$-alkenyl, $C_2$-$C_4$-alkynyl or $C_7$-$C_{12}$-aralkyl, eg. methyl, ethyl, propyl, i-propyl, butyl, i-butyl, s-butyl, pentyl, hexyl, heptyl, cyclobutyl, cyclopentyl, cyclohexyl, cycloheptyl, cyclooctyl, allyl, but-2-ynyl, benzyl or phenethyl.

Preferred ureas of the formula I are those in which $R^1$ is $C_1$-$C_4$-alkyl, preferably methyl, and $R^2$ is hydrogen, $C_1$-$C_4$-alkyl, preferably methyl, or $C_1$-$C_4$-alkoxy, preferably methoxy. Other preferred ureas are those which have this structure and in which $R^3$ and/or $R^4$ are $C_3$-$C_8$-cycloalkylthiocarbonyl or $C_4$-$C_8$-alkyl.

The substituted ureas of the formula I are obtained by a process in which a substituted aniline of the formula

where $R^3$ and $R^4$ have the above meanings, (a) is reacted with phosgene or diphosgene, and the product is then reacted with an amine of the formula $$HNR^1R^2 \qquad (III),$$

where $R^1$ and $R^2$ have the above meanings, or (b) is reacted with a carbamyl halide of the formula $$Hal-CO-NR^1R^2 \qquad (IV),$$

where $R^1$ and $R^2$ have the above meanings and Hal is halogen.

Furthermore, substituted ureas of the formula I can be obtained by reacting a benzoyl halide of the formula

where $R^3$ and $R^4$ have the above meanings and Hal is halogen, with an alkali metal azide or a trialkylsilyl azide, converting the resulting acid azide to the corresponding isocyanate and reacting the latter with an amine of the formula III.

Substituted ureas of the formula I in which $R^1$ is $C_1$-$C_4$-alkyl and $R^2$, $R^3$ and $R^4$ have the above meanings can also be obtained by reacting a substituted aniline of the formula II with an isocyanate of the formula $$R^1NCO \qquad (VI)$$

where $R^1$ is $C_1$-$C_4$-alkyl.

The reactions described above are preferably carried out in the presence of a suitable solvent or diluent. These include virtually all inert organic solvents, in particular aromatic and aliphatic hydrocarbons, eg. naphtha, gasoline, toluene, pentane, hexane, cyclohexane and petroleum ether, aromatic and aliphatic halohydrocarbons, eg. methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene, aromatic and aliphatic nitro hydrocarbons, eg. nitrobenzene, nitroethane and o-, m- and p-nitrotoluene, nitriles, eg. acetonitrile, butyronitrile and isobutyronitrile, ethers, eg. diethyl ether, di-n-propyl ether, tetrahydrofuran and dioxane, esters, eg. ethyl acetoacetate, ethyl acetate and isobutyl acetate, ketones, eg. acetone, methyl ethyl ketone, methyl isopropyl ketone and methyl isobutyl ketone, and amides, eg. methylformamide and dimethylformamide, as well as mixtures of these solvents.

The reaction of an aniline of the formula II with an amine of the formula III can be very readily carried out by a method in which a substituted aniline of the formula II is first converted to the corresponding isocyanate using an excess of phosgene (cf. Houben-Weyl 8 (1952), 122–123; Methodicum Chimicum 6 (1974), 780), and the isocyanate is then reacted with not less than an equivalent amount of amine of the formula III, in the presence or absence of a solvent, at from −10° to +150° C., preferably 20° to 120° C., by a continuous or batchwise procedure.

To carry out the reaction in which a substituted aniline of the formula II is reacted with a carbamyl halide of the formula IV, the latter is reacted in an excess of as much as 50% (mole % or % by weight), in the presence or absence of a solvent and of an acid acceptor, at from −10° to 150° C., preferably from 20° to 120° C., by a continuous or batchwise procedure (Houben-Weyl, Methoden der organischen Chemie 8 (1952), 160–161).

The acid acceptor used can be any conventional one, but is preferably an alkali metal hydroxide, an alkali metal carbonate, an alkali metal alcoholate or a tertiary organic base. Specific examples of particularly suitable compounds are sodium hydroxide, sodium bicarbonate, sodium methylate, triethylamine, pyridine, trimethylamine, alpha- and beta-picoline, lutidine, N,N-dimethylaniline, N,N-dimethylcyclohexylamine, quinoline, tri-n-propylamine, tri-n-butylamine and acridine.

To carry out the process starting from a benzoyl halide of the formula V, 0.1 mole of the benzoyl halide, preferably benzoyl chloride, is reacted with from 0.1 to 0.4 mole of an alkali metal azide or an excess of a trimethylsilyl azide to give the corresponding phenyl isocyanate. This is isolated as a crude product, if necessary by evaporating down the reaction mixture, and is mixed with not less than an equimolar amount of an amine of the formula III for the further reactions, in the presence or absence of a solvent. Preferably, the benzoyl halide of the formula V is reacted with a trimethylsilyl azide, the product is then converted to the corresponding isocyanate by heating (Synthesis 1972, pages 551–553) and the isocyanate is then reacted with an amine in the presence or absence of a solvent at from −10° to +150° C., preferably from 20° to 120° C., by a continuous or batchwise procedure.

In the version of the process which is based on the reaction of an aniline with an isocyanate, a substituted aniline of the formula II is reacted with an excess of as much as 50% (mole % or % by weight) of an isocyanate of the formula VI, in the presence or absence of a solvent, at from −10° to +150° C., preferably from 20° to 120° C., by a continuous or batchwise procedure (Houben-Weyl, Methoden der org. Chemie, 8 (1952), 157–159).

In all versions of the process, end products which are precipitated from the reaction mixture are isolated by filtering them off under suction and then purifying them by recrystallization or chromatography; otherwise, they are isolated by evaporating the reaction mixture to dryness under reduced pressure, and purifying the residue by recrystallization or chromatography.

The substituted anilines of the formula II which can be used as starting materials are novel. They can be obtained by reducing nitrobenzoic acid thiolesters of the formula

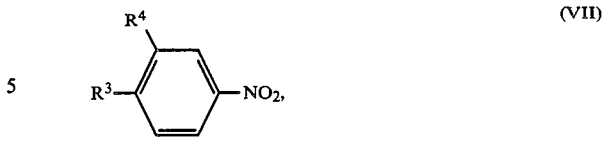

where $R^3$ and $R^4$ have the above meanings, by catalytic hydrogenation in the presence of, as a catalyst, a metal of sub-group 8, and in the presence of a solvent. The course of this reaction is surprising since, according to the literature, the reduction of benzoic acid thiolesters with Raney nickel and hydrogen leads to cleavage, so that benzyl alcohols and mercaptans are formed (Houben-Weyl, Methoden der organischen Chemie, vol. 8, pages 644–645, Georg-Thieme-Verlag, Stuttgart, 4th edition, 1952).

The catalytic hydrogenation is carried out under conventional conditions. Suitable catalysts are all metals of sub-group 8 in finely divided form or on a carrier or in the form of a compound. Mixtures may also be used. Preferred catalysts are nickel, platinum and palladium.

Suitable solvents are all inert ones, in particular alcohols, eg. methanol, ethanol and propanol, ethers, eg. tetrahydrofuran, and ketones and esters.

The reaction temperature can vary from 0° to 200° C., preferably from room temperature to 80° C. The reaction time is from 2 hours to 2 days, preferably 6 to 36 hours.

The nitrobenzoic acid thiol esters of the formula VII can be prepared by a conventional method (Houben-Weyl, Methoden der organischen Chemie, vol. 9, pages 754–755, Georg-Thieme-Verlag, Stuttgart, 4th edition, 1955).

EXAMPLE 1

(a) 20.8 g of 1,2-dimethyl-n-propylmercaptan, 50 ml of ethylene chloride and 22.2 g of triethylamine were initially taken at room temperature, 48.4 g of 2-chloro-4-nitrobenzoyl chloride were added dropwise at 10°–20° C., while cooling with ice water, the mixture was kept at about 15° C. for 2 hours and stirring was continued overnight at room temperature. The mixture was filtered under suction, and the filtrate was washed with water, dilute hydrochloric acid and dilute NaHCO₃ solution and again with water, dried and evaporated down to give 49.3 g of 1,2-dimethyl-n-propyl 2-chloro-4-nitrothiobenzoate of $n_D^{25}$ 1.5678.

(b) 40 g of the resulting product in 150 ml of tetrahydrofuran were hydrogenated for 15 hours at 50° C., using 8 g of Raney nickel and $H_2$ under 200 bar. The catalyst was separated off, and the mixture was then evaporated down to give 33.3 g of 1,2-dimethyl-n-propyl 2-chloro-4-aminothiobenzoate of melting point 43°–46° C.

(c) 8.24 g of the resulting product in 80 ml of toluene were initially taken, a total of 3 g of methyl isocyanate in toluene was added dropwise, and the mixture was kept at 40° C. for 2 hours. Evaporating down the mixture gave 10 g of crude product, which was about 80% pure. Purification by column chromatography (over silica gel, using toluene and toluene/acetone) gave 5 g of N-[3-chloro-4-(1,3-dimethyl-n-propylmercaptocarbonyl)-phenyl]-N'-methylurea of melting point 89°–95° C. (compound no. 1).

EXAMPLE 2

(a) 34.8 g of cyclohexylmercaptan, 200 ml of 1,1,1-trichloroethane and 36.3 g of triethylmercaptan were initially taken, 72.6 g of 2-chloro-4-nitrobenzoyl chloride in 100 ml of 1,1,1-trichloroethane were then added dropwise at 10°–20° C., and the mixture was kept for 2 hours at 15° C. and overnight at room temperature. The mixture was filtered under suction, and the filtrate was washed thoroughly with water, dried and evaporated down to give 81.7 g of cyclohexyl 2-chloro-4-nitrothiobenzoate of refractive index $n_D^{25}$ 1.5914.

(b) 210 g of the resulting product were dissolved in 2 liters of tetrahydrofuran, 15 g of Raney nickel were added, and hydrogenation was carried out for 15 hours at 50° C., using hydrogen under 200 atm. The catalyst was then separated off, and the mixture was evaporated down to give 179.5 g of cyclohexyl 2-chloro-4-aminothiobenzoate of melting point 97°–100° C.

(c) 6.74 g of the resulting product were dissolved in 60 ml of toluene and 10 ml of pyridine, and 3.4 g of N-methyl-N-methoxycarbamyl chloride were then added dropwise. Owing to the exothermic reaction, the temperature increased to 29° C. The mixture was then kept at 40° C. for 2 hours, after which it was filtered under suction, and the filtrate was washed thoroughly with water and dilute hydrochloric acid, dried and evaporated down to give 6 g of N-(3-chloro-4-cyclohexylmercaptocarbonylphenyl)-N'-methyl-N'-methoxyurea (compound no. 37).

EXAMPLE 3

(a) 107.8 g of cyclohexyl 2-chloro-4-aminothiobenzoate in 350 ml of 1,1,1-trichloroethane were added dropwise to a solution of 90 g of phosgene in 150 ml of 1,1,1-trichloroethane at from −10° to −15° C. The mixture was heated gradually, and was then refluxed for 3 hours. Evaporating down gave 122.1 g of cyclohexyl 2-chloro-4-isocyanatothiobenzoate of melting point 60°–65° C.

(b) 20 g of cyclohexyl 2-chloro-4-isocyanatothiobenzoate in 80 ml of toluene were added dropwise to excess aqueous dimethylamine solution at room temperature. The mixture was kept at room temperature, stirred overnight and then filtered under suction. 16.3 g of N-(3-chloro-4-cyclohexylmercaptocarbonylphenyl)-N',N'-dimethylurea (compound no. 35) were obtained.

The following compounds of the formula I can be prepared by similar methods:

| Compound no. | $R^1$ | $R^2$ | $R^3$ | $R^4$ | M.p. (°C.)/$n_D$ |
|---|---|---|---|---|---|
| 1 | $CH_3$ | H | —C(O)—S—CH($CH_3$)—CH($CH_3$)$_2$ | Cl | 89–95 |
| 2 | $CH_3$ | $CH_3$ | " | Cl | 115–119 |
| 3 | $CH_3$ | $OCH_3$ | " | Cl | $n_D^{25}$ 1.5756 |
| 4 | $CH_3$ | H | H | —C(O)—S—CH($CH_3$)—CH($CH_3$)$_2$ | 71–73 |
| 5 | $CH_3$ | $CH_3$ | H | " | 69–71 |
| 6 | $CH_3$ | $OCH_3$ | H | " | $n_D^{25}$ 1.5607 |
| 7 | $CH_3$ | $CH_3$ | Cl | " | |
| 8 | $CH_3$ | H | Cl | " | |
| 9 | $CH_3$ | $OCH_3$ | Cl | " | |
| 10 | $CH_3$ | H | —C(O)—S—C($CH_3$)$_2$—$CH_2$—$CH_3$ | H | 104–107 |
| 11 | $CH_3$ | $CH_3$ | " | H | 136–139 |
| 12 | $CH_3$ | $OCH_3$ | " | H | $n_D^{25}$ 1.5738 |
| 13 | $CH_3$ | H | H | —C(O)—S—C($CH_3$)$_2$—$CH_2$—$CH_3$ | |
| 14 | $CH_3$ | $CH_3$ | H | " | |
| 15 | $CH_3$ | $OCH_3$ | H | —C(O)—S—C($CH_3$)$_2$—$CH_2$—$CH_3$ | |
| 16 | $CH_3$ | H | —C(O)—S—CH($CH_3$)$_2$ | Cl | |
| 17 | $CH_3$ | $CH_3$ | " | Cl | |
| 18 | $CH_3$ | $OCH_3$ | " | Cl | |
| 19 | $CH_3$ | H | —C(O)—S—$CH_3$ | Cl | |
| 20 | $CH_3$ | $CH_3$ | " | Cl | |
| 21 | $CH_3$ | $OCH_3$ | " | Cl | |

-continued

| Compound no. | R¹ | R² | R³ | R⁴ | M.p. (°C.)/$n_D$ |
|---|---|---|---|---|---|
| 22 | CH₃ | H | −C(=O)−S−CH₂−CH(CH₃)−CH₂−C(CH₃)₃ | H | |
| 23 | CH₃ | CH₃ | " | H | |
| 24 | CH₃ | OCH₃ | " | H | |
| 25 | CH₃ | H | −C(=O)−S−CH₂−C(CH₃)=CH₂ | Cl | |
| 26 | CH₃ | CH₃ | " | Cl | $n_D^{25}$ 1.5945 |
| 27 | CH₃ | OCH₃ | " | Cl | $n_D^{25}$ 1.6082 |
| 28 | CH₃ | H | Cl | −C(=O)−S−CH₂−CH=CH₃ | |
| 29 | CH₃ | CH₃ | Cl | " | |
| 30 | CH₃ | OCH₃ | Cl | " | |
| 31 | CH₃ | H | −C(=O)−S−CH₂−C(CH₃)₃ | Cl | |
| 32 | CH₃ | CH₃ | " | Cl | |
| 33 | CH₃ | OCH₃ | " | Cl | |
| 34 | CH₃ | H | −C(=O)−S−cyclohexyl | Cl | 143–147 |
| 35 | CH₃ | CH₃ | " | Cl | 178–181 |
| 36 | C₂H₅ | C₂H₅ | " | Cl | 178–180 |
| 37 | CH₃ | CH₃O | " | Cl | 94–96 |
| 38 | CH₃ | H | −C(=O)−S−cyclohexyl | H | 160–165 |
| 39 | CH₃ | CH₃ | " | H | |
| 40 | C₂H₅ | C₂H₅ | " | H | |
| 41 | CH₃ | CH₃O | " | H | 139–141 |
| 42 | CH₃ | H | Cl | −C(=O)−S−cyclohexyl | 156–160 |
| 43 | CH₃ | CH₃ | Cl | " | 150–154 |
| 44 | CH₃ | CH₃O | Cl | " | 101–110 |
| 45 | CH₃ | H | H | −C(=O)−S−cyclohexyl | 152–155 |
| 46 | CH₃ | CH₃ | H | " | |
| 47 | CH₃ | CH₃O | H | −C(=O)−S−cyclohexyl | $n_D^{25}$ 1.5719 |
| 48 | CH₃ | H | −C(=O)−S−cyclopentyl | Cl | |
| 49 | CH₃ | CH₃ | " | Cl | |
| 50 | CH₃ | CH₃O | " | Cl | |

-continued

| Compound no. | R¹ | R² | R³ | R⁴ | M.p. (°C.)/$n_D$ |
|---|---|---|---|---|---|
| 51 | CH₃ | H | " | H | 189–195 |
| 52 | CH₃ | CH₃ | " | H | 89–99 |
| 53 | CH₃ | CH₃O | " | H | |
| 54 | CH₃ | H | Cl | 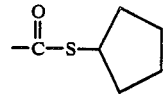 | |
| 55 | CH₃ | CH₃ | Cl | " | |
| 56 | CH₃ | CH₃O | Cl | " | |
| 57 | CH₃ | H | 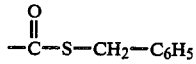 | H | 174–178 |
| 58 | CH₃ | CH₃ | " | H | |
| 59 | CH₃ | CH₃O | " | H | 53–65 |
| 60 | CH₃ | H | 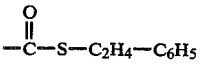 | H | |
| 61 | CH₃ | CH₃ | " | H | |
| 62 | CH₃ | CH₃O | " | H | |
| 63 | CH₃ | H | 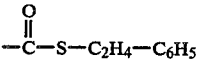 | Cl | 143–147 |
| 64 | CH₃ | CH₃ | " | Cl | 131–134 |
| 65 | CH₃ | CH₃O | " | Cl | $n_D^{25}$ 1.611 |
| 66 | CH₃ | H | H | 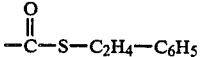 | 145–149 |
| 67 | CH₃ | CH₃ | H | " | 150–152 |
| 68 | CH₃ | CH₃O | H | " | 85–88 |
| 69 | CH₃ | H | 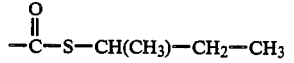 | 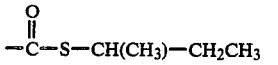 | |
| 70 | CH₃ | CH₃ | " | " | |
| 71 | CH₃ | CH₃O | " | " | |
| 72 | CH₃ | CH(CH₃)—C≡CH | 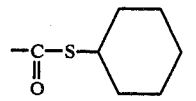 | Cl | 135–138 |
| 73 | H | 4-chlorophenyl | 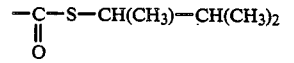 | Cl | 152–154 |
| 74 | H | 2,6-dichlorophenyl | " | Cl | 187–190 |
| 75 | CH₃ | CH₃ | 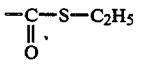 | Cl | |
| 76 | CH₃ | H | H | Cl | |
| 77 | CH₃ | CH₃O | H | Cl | |
| 78 | CH₃ | CH₃ | H | 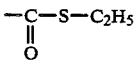 | |
| 79 | CH₃ | H | H | " | |
| 80 | CH₃ | CH₃O | H | " | |
| 81 | CH₃ | CH₃ | H | 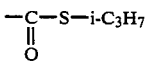 | |
| 82 | CH₃ | H | H | " | |

-continued

| Compound no. | R¹ | R² | R³ | R⁴ | M.p. (°C.)/$n_D$ |
|---|---|---|---|---|---|
| 83 | CH₃ | CH₃ | H | " | |
| 84 | CH₃ | CH₃ | —C(=O)—S—CH(CH₃)C₂H₅ | Cl | |
| 85 | CH₃ | H | " | Cl | |
| 86 | CH₃ | CH₃O | " | Cl | |
| 87 | CH₃ | CH₃O | —C(=O)—S—[CH(CH₃)]₂—CH₃ | —C(=O)—S—[CH(CH₃)]₂—CH₃ | $n_D^{25}$ 1.5685 |
| 88 | CH₃ | H | —C(=O)—S—[CH(CH₃)]₂—CH₃ | —C(=O)—S—[CH(CH₃)]₂—CH₃ | 182–184 |

Analogously to the methods described in Examples 1b and 2b, the following substituted anilines of the formula II may be obtained by reduction of the corresponding nitrobenzoic acid thiol esters of the formula VII:

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by

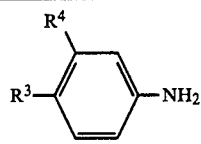
(II)

| R³ | R⁴ | Reduction period [h] | Yield [%] | M.p. [°C.]/$n_D$ |
|---|---|---|---|---|
| —CH(CH₃)—C(CH₃)₂ | Cl | 15 | 92 | 43–46 |
| —C(CH₃)₂—C₂H₅ | H | 15 | 91 | 57–60 |
| cyclohexyl | Cl | 15 | 95 | 77–81 |
| cyclohexyl | H | 15 | 91 | 85–87 |
| H | —CH(CH₃)—C(CH₃)₂ | 15 | 96 | $n_D^{25}$ 1.5860 |
| —CH₂—C₆H₅ | H | 15 | 74 | 81–105 |
| H | cyclohexyl | 15 | 93 | 38–43 |
| Cl | cyclohexyl | 15 | 90 | 74–77 |
| —C₂H₄—C₆H₅ | Cl | 15 | 94 | 143–146 |
| cyclopentyl | Cl | 30 | 77 | 101–103 |
| Cl | cyclopentyl | 15 | 91 | 69–72 |
| cyclopentyl | H | 60 | 86 | 80–95 |

The substituted ureas of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 10 parts by weight of compound no. 6 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 34 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 37 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 3 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 34 is intimately mixed with 95 parts by weight of particulate kaolin. A dust is obtained containing 5% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and their growth stage, and varies from 0.05 to 5 kg/ha and more, but is preferably from 0.1 to 1.0 kg/ha.

The herbicidal action of urea derivatives of the formula I on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. No covers were placed on the pots in this treatment method. The application rates for postemergence treatment varied from ingredient to ingredient, and were for example from 0.125 to 1.0 kg of active ingredient per hectare.

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus spp., Arachys hypogae, Cassia tora, Chenopodium album, Euphorbia heterophylla, Galium aparine, Glycine max., Ipomoea spp., Lamium amplexicaule, Mercurialis annua, Oryza sativa, Sesbania exaltata, Sinapis alba, Solanum nigrum, Triticum aestivum, and Zea mays.

On preemergence application of 3.0 kg/ha, for example active ingredients 34 and 37 had a good herbicidal action.

On postemergence application of 0.125 kg/ha, for instance active ingredients 6 and 37 combated unwanted broadleaved plants without damaging rice and wheat. Compound no. 1 was selective in soybeans at an application rate of 0.25 kg/ha, and compound no. 2 was selective in Indian corn at the same rate. Compounds nos. 34, 35, 65 and 72, applied at the same rate, selectively combated broadleaved weeds in groundnuts and wheat, and compound no. 44 was selectively active on broadleaved weeds in wheat and Indian corn. Compounds nos. 3 and 4, for example at 0.5 kg/ha, combated broadleaved weeds in groundnuts.

In view of the numerous application methods possible, the compounds according to the invention, or agents containing them, may be used in a further number of crops for removing unwanted plants. The following crops may be mentioned by way of example:

| Botanical name | Common name |
| --- | --- |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora) | coffee plants |
| Coffea liberica | |
| Cucumis melo | melons |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Petroselinum crispum | parsley |
| spp. tuberosum | |
| Picea aries | Norway spruce |
| Abies alba | fir trees |
| Pinus spp. | pine trees |
| Pisum sativum | English peas |
| Prunus avium | cherry trees |
| Pronus domestica | plum trees |

-continued

| Botanical name | Common name |
| --- | --- |
| Pronus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the substituted ureas of the formula I may be mixed and applied together with numerous other herbicidal active ingredients. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A substituted urea of the formula

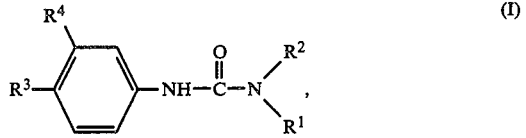

(I)

where $R^1$ is hydrogen or $C_1$-$C_4$-alkyl, $R^2$ is hydrogen, $C_1$-$C_4$-alkyl, $C_1$-$C_4$-alkoxy, $C_2$-$C_4$-alkenyl, $C_2$-$C_4$-alkynyl, unsubstituted or $C_1$-$C_4$-alkyl-substituted $C_3$-$C_7$-cycloalkyl, or phenyl which is unsubstituted or substituted by halogen or by $C_1$-$C_4$-haloalkyl, $R^3$ is hydrogen, halogen or a radical —CO—S—R where R is $C_1$-$C_{10}$-alkyl, $C_3$-$C_8$-cycloalkyl, $C_2$-$C_4$-alkenyl, $C_2$-$C_4$-alkynyl or $C_7$-$C_{12}$-aralkyl and $R^4$ is hydrogen, halogen or a radical —CO—S—R, where R is $C_1$-$C_{10}$-alkyl, $C_3$-$C_8$-cycloalkyl, $C_2$-$C_4$-alkenyl, $C_2$-$C_4$-alkynyl or $C_7$-$C_{12}$-aralkyl, with the proviso that one or both of the substituents $R^3$ and $R^4$ are —CO—S—R.

2. A substituted urea of the formula I as set forth in claim 1, where $R^1$ is $C_1$-$C_4$-alkyl and $R^2$ is hydrogen, $C_1$-$C_4$-alkyl or $C_1$-$C_4$-alkoxy.

3. A substituted urea of the formula I as set forth in claim 1, where $R^1$ is $C_1$-$C_4$-alkyl, $R^2$ is $C_1$-$C_4$-alkyl or $C_1$-$C_4$-alkoxy and $R^3$ is $C_3$-$C_8$-cycloalkylthiocarbonyl or $C_4$-$C_8$-alkylthiocarbonyl.

4. A substituted urea of the formula I as set forth in claim 1, where $R^1$ is $C_1$-$C_4$-alkyl, $R^2$ is $C_1$-$C_4$-alkyl or $C_1$–$C_4$-alkoxy and $R^4$ is $C_3$–$C_8$-cycloalkylthiocarbonyl or $C_4$–$C_8$-alkylthiocarbonyl.

5. A substituted urea of the formula I as set forth in claim 1, where $R^1$ is methyl, $R^2$ is methoxy, $R^3$ is cyclohexylthiocarbonyl and $R^4$ is chlorine.

6. A substituted aniline of the formula

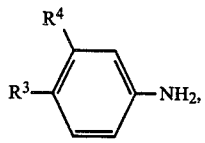

(II)

where $R^3$ is hydrogen, halogen or a radical —CO—S—R, R denoting $C_1$–$C_{10}$-alkyl, $C_3$–$C_8$-cycloalkyl, $C_2$–$C_4$-alkenyl, $C_2$–$C_4$-alkynyl or $C_7$–$C_{12}$-aralkyl, and $R^4$ is hydrogen, halogen or a radical —CO—S—R, R denoting $C_1$–$C_{10}$-alkyl, $C_3$–$C_8$-cycloalkyl, $C_2$–$C_4$-alkenyl, $C_2$–$C_4$-alkynyl or $C_7$–$C_{12}$-aralkyl, with the proviso that one or both of the substituents $R^3$ and $R^4$ are —CO—S—R.

7. A herbicidal composition containing inert additives and a herbicidally effective amount of a substituted urea of the formula I as defined in claim 1.

8. A herbicidal composition containing inert additives and a herbicidally effective amount of a substituted urea of the formula I as defined in claim 3.

9. A herbicidal composition containing inert additives and a herbicidally effective amount of a substituted urea of the formula I as defined in claim 4.

10. A process for combating the growth of unwanted plants, wherein the unwanted plants or the area to be kept free from unwanted plant growth are treated with a herbicidally effective amount of a substituted urea of the formula I as defined in claim 1.

* * * * *